United States Patent [19]

Sekine

[11] 4,047,438
[45] Sept. 13, 1977

[54] LIQUID QUANTITATIVE DISPENSING APPARATUS

[76] Inventor: Teruaki Sekine, 1-1 Tsukiji 5-chome, Chuo, Tokyo, Japan

[21] Appl. No.: 672,170

[22] Filed: Mar. 31, 1976

[30] Foreign Application Priority Data

Apr. 4, 1975  Japan ............................ 50-46509[U]

[51] Int. Cl.$^2$ .............................................. B01L 3/02
[52] U.S. Cl. .................................. 73/423 A; 73/425.6
[58] Field of Search ............... 73/423, 425.4 P, 425.6; 141/21, 25, 26, 27, 238, 242

[56] References Cited

U.S. PATENT DOCUMENTS

| 3,498,342 | 3/1970 | Sanderson | 141/238 |
| 3,650,306 | 3/1972 | Lancaster | 222/263 |
| 3,807,235 | 4/1974 | Lefkovits | 73/425.6 |

*Primary Examiner*—S. Clement Swisher
*Attorney, Agent, or Firm*—George B. Oujevolk

[57] ABSTRACT

Liquid quantitative dispensing apparatus for withdrawing liquid like a syringe into a plurality of pipettes arranged in rows, by simultaneously pressing and releasing cap-like projections formed of flexible material and dispensing the liquid to test tubes and the like.

3 Claims, 4 Drawing Figures

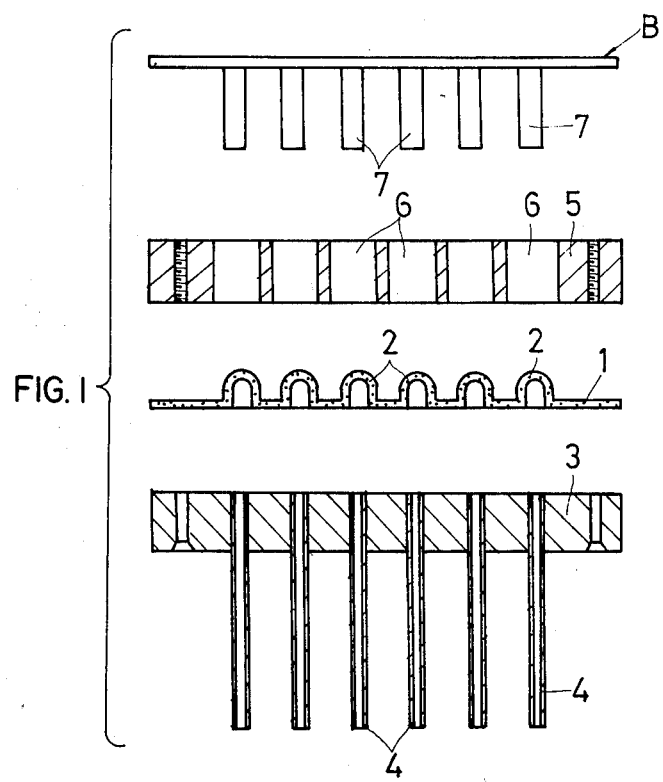
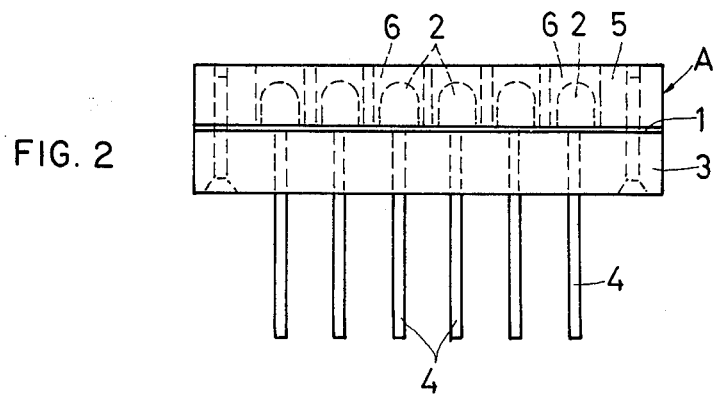

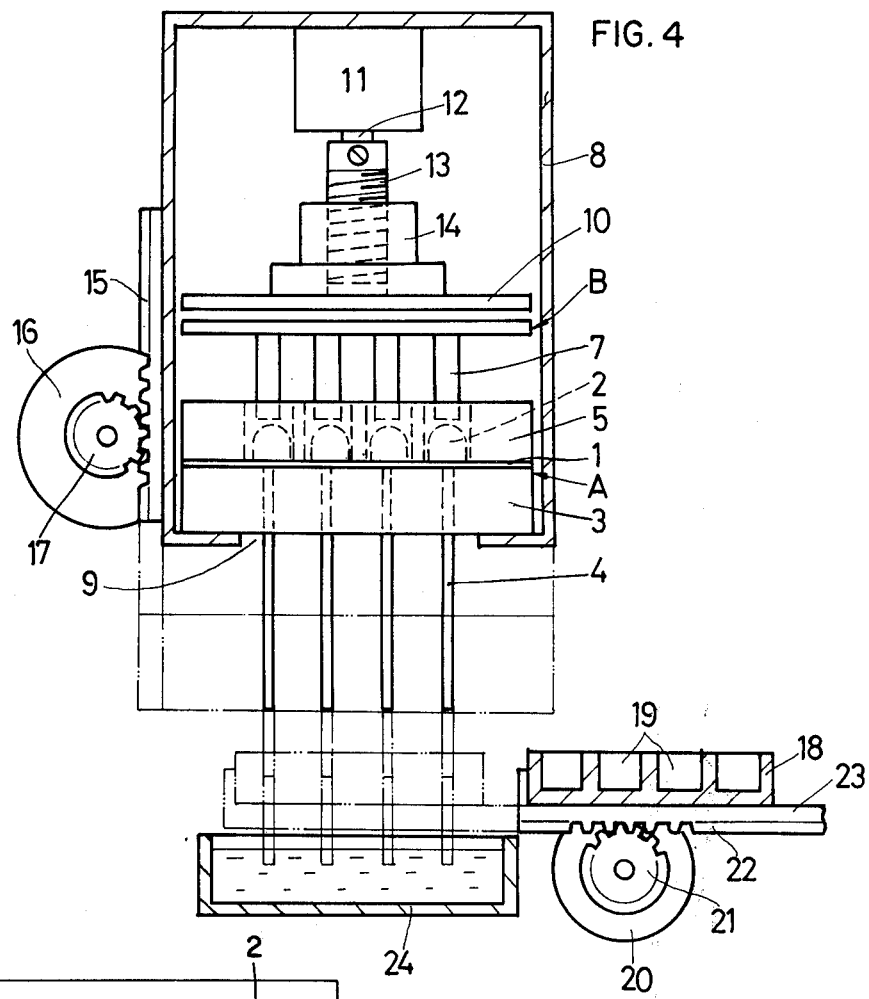
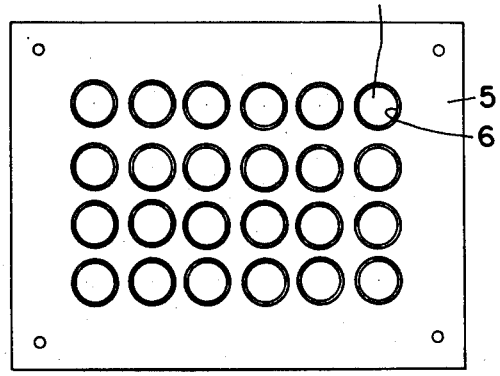

LIQUID QUANTITATIVE DISPENSING APPARATUS

SUMMARY OF THE INVENTION

I. Field of the Invention

This invention relates generally to a laboratory analyzing and titrating apparatus and more particularly to an apparatus for quantitatively dispensing predetermined reproducible microquantities of liquid from a liquid source to partitioned liquid wells.

II. Prior Art

Conventionally, in this type of dispensing apparatus a vacuum pump has been used to obtain suction force for withdrawing liquid from a pipe by using a rubber diaphragm. In such a method, however, it often occurs that the diaphragm becomes damaged or, in case of locking screws being loosened, the adjustment of suctioning operation gets out of order because of the vacuum suctioning method so as to cause the withdrawing the total amount of expensive test chemicals or blood in one moment, thus making it impossible to expect a smooth dispensing operation and, moreover, the apparatus become complicated in construction and accordingly expensive in the cost.

The present invention eliminates the aforementioned drawbacks and aims at providing a dispensing apparatus that is compact, desk-type, particularly simple in construction and inexpensive. Another object of the present invention is to obtain apparatus capable of quantitatively dispensing liquid to each of the liquid wells.

BRIEF EXPLANATION OF THE DRAWINGS

The accompanying drawings show one preferred embodiment of the liquid quantitative dispensing apparatus of the present invention, wherein:

FIG. 1 is an elevational view in longitudinal section showing the entire body in its disassembled state;

FIG. 2 is a front view of the main parts in assembly;

FIG. 3 is a plan view thereof; and

FIG. 4 is a side view in longitudinal section of a liquid dispensing machine employing an apparatus according to this invention.

DETAILED EXPLANATION OF THE INVENTION

This invention relates to liquid quantitative dispensing apparatus for use in any analyzing operation requiring microquantities of liquid quantitatively and simultaneously in a number of containers such as needles or pipettes.

According to the inventive concept a flexible board-like member made of rubber or the like, having a plurality of cap-like projections arranged in rows with a small space therebetween is provided, and, under the flexible board-like member a lower board having a plurality of pipettes which are held in said lower board corresponding in number to the cap-like projections is positioned. A guide board is fixed on the flexible board-like member which has bores corresponding in number to the cap-like projections and into which these projections may be inserted loosely. The main body of the apparatus is assembled by assembling the aforementioned lower board, the flexible board-like member and the guide board, and also using a keep plate having push bars arranged in rows for pressing the cap-like projections of the said main body.

The accompanying drawings show one preferred embodiment of the liquid quantitative dispensing apparatus of the present invention, wherein 1 is a flexible board like member having a plurality of cap-like projections 2 arranged lengthwise and crosswise thereon with a small space between each of them. The flexible board like member is made of rubber in the embodiment shown herein, but it can also be formed of flexible synthetic resin. The reference numeral 3 shows a lower board to be positioned under the flexible board-like member 1, said lower board being provided with a plurality of pipettes 4 held therein with the upper aperture of the pipettes disposed in operative alignment with the aforementioned cap-like projections 2. There is a guide board 5 which is positioned above the flexible board like member 1, said guide board 5 is provided with the same number of bores 6 as the number of the cap-like projections 2 into which bores can be loosely inserted. The above-mentioned flexible board like member, lower board 3 and the guide board 5 together form a main body A against which the present invention has a keep plate B. The keep plate B is provided with push bars 7 for pushing the cap-like projections 2, and by inserting the push bars into the bores 6 and pressing the projections 2 to exhaust the air therein and thereafter by releasing the push bars 7 liquid can be withdrawn into the pipettes 4 from a liquid reservoir. Thus, the apparatus of this invention withdraws liquid like a syringe and squirts the liquid to a number of liquid wells.

In the drawings, there is shown a housing 8 containing the main body A and the keep plate B. There is an opening 9 formed in the lower surface of the housing 8, and a push plate 10 for pushing the keep plate B the push bars 7 which move against the restitution power of the caplike projections, said push plate 10 being fixed to an internal thread member 14 which engages with the external thread 13 provided on the axle 12 of the motor 11. A rack 15 is provided on the side surface of the housing 8 and it engages with the pinion 17 which is rotated by the motor 16. Use is made of a dispensing plate 18 having a plurality of wells 19 cut therein and which is placed on a rack member 23. The rack member 23 can slide by means of the rack 22 which engages with the pinion 21 which is rotated by the motor 20.

The apparatus of the present invention operates to lower the whole body by means of motor 16 and the other mechanism, and when the keep plate B is pressed downwards by the motor 11 and the other mechanism under the condition in which the pipettes 4 remain in contact with the liquid the push bars 7 push the cap-like projections 2 thereby allowing the air in the pipettes 4 to exhaust. And when the keep plate B is released the liquid in the reservoir is withdrawn into the pipettes 4 by the suction force produced when the cap-like projections 2 are restored to their original state. Then, the entirety of the apparatus is driven upwards and the dispensing plate 18 is moved to a position thereunder. When the keep plate B is pushed downwards in the state just described above the liquid in the pipettes 4 is supplied into each of the wells 19.

The apparatus according to this invention are capable of dispensing liquid by means of a quite simple mechanism as described and the dispensing quantity is very accurate, avoiding the possibility of failure and yet providing the advantage of producing the apparatus relatively inexpensively.

What is claimed is:

1. Liquid quantitative dispensing apparatus comprising a flexible board-like member having a plurality of cap-like projections arranged in rows lengthwise and crosswise thereon with a small space between each of said projections, a lower board positioned under the said flexible board-like member and having a plurality of aligned pipettes held therein which correspond in number with said projections, a guide board positioned on the said flexible board-like member and having bores to loosely receive said cap-like projections, the said guide board, flexible board-like member and said lower board forming together the main apparatus body, and a keep plate having push bars disposed thereunder so as to be inserted into the said bores of the said guide board to press said cap-like projections.

2. Liquid quantitative dispensing apparatus according to claim 1, wherein the said flexible board-like member is formed of rubber material.

3. Liquid quantitative dispensing apparatus according to claim 1, wherein the said flexible board-like member is formed of soft elastic synthetic resin.